United States Patent [19]

Literati Nagy et al.

[11] Patent Number: 5,216,023
[45] Date of Patent: Jun. 1, 1993

[54] POLYUNSATURATED FATTY ACID DERIVATIVES, PHARMACEUTICAL COMPOSITIONS CONTAINING THE SAME, METHOD FOR THE PREPARATION THEREOF, AND THEIR USE AS MEDICAMENT

[75] Inventors: Péter Literati Nagy; György Këri; Mária Boross; Gábor Németh; Jenö Szilbereky; Ildikó Szilágyi, all of Budapest, Hungary

[73] Assignee: Folligen Budapest Ltd., Budapest, Hungary

[21] Appl. No.: 576,393

[22] PCT Filed: Jan. 16, 1990

[86] PCT No.: PCT/HU90/00004

§ 371 Date: Sep. 12, 1990

§ 102(e) Date: Sep. 12, 1990

[87] PCT Pub. No.: WO90/08130

PCT Pub. Date: Jul. 26, 1990

[30] Foreign Application Priority Data

Jan. 17, 1989 [HU] Hungary ............................. 168/89

[51] Int. Cl.$^5$ ............................................. A61K 31/24
[52] U.S. Cl. ........................................ 514/538; 554/56; 554/63; 554/127; 562/552
[58] Field of Search ................ 260/404.5 A, 404; 514/538; 562/552; 554/56, 63, 121

[56] References Cited

U.S. PATENT DOCUMENTS

| | | | |
|---|---|---|---|
| 2,463,799 | 3/1949 | Kester et al. | 260/404 |
| 3,758,525 | 9/1973 | Yoshida et al. | 260/404 |
| 3,927,047 | 12/1975 | Ichikawa et al. | 260/404 |
| 3,985,722 | 10/1976 | Yoshida et al. | 260/404 |

FOREIGN PATENT DOCUMENTS

63-230630 9/1988 Japan.
63-230663 9/1988 Japan.

OTHER PUBLICATIONS

Chemical Abstracts, vol. 113, #7, p. 59, 1990, 52513r.
Chem Abstracts 110:1415326.
Chem Abstracts 111:1208922.

*Primary Examiner*—Jose G. Dees
*Assistant Examiner*—Deborah D. Carr
*Attorney, Agent, or Firm*—Herbert Dubno; Jonathan Myers

[57] ABSTRACT

The compounds of the Formula (I)

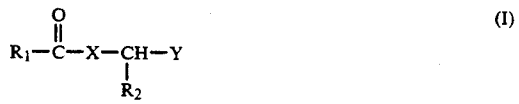

wherein
$R_1$ is a $C_{18-24}$alkenyl containing at least two double bonds, or $-(CH_2)_n-CH(NH_2)_m-COOH$
X is O, NH or $C_{1-4}$alkyl-N,
Y is $CONH_2$, COOH or COOMe, wherein Me is hydrogen metal, and
$R_2$ is a side chain of a any amino acid except L-GLU or L-ASP at α-position or a group of Formula $$-(CH_2)_k-C_6H_3-(A)_2 \qquad (II),$$

$$-(CH_2)_n-X-(CH_2)_m-X-M \qquad (III)$$

wherein
k is zero or an integer of 1,
n is zero or an integer of 1 to 3,
m is zero or an integer of 1 to 4,
A is hydroxyl or one A is hydroxyl and the other A is hydrogen.
M is H or $R_1$—CO and
X and $R_1$ are as defined above and their salts having tyrosine kinase inhibitor activity can be used as antitumor agents.

4 Claims, No Drawings

POLYUNSATURATED FATTY ACID DERIVATIVES, PHARMACEUTICAL COMPOSITIONS CONTAINING THE SAME, METHOD FOR THE PREPARATION THEREOF, AND THEIR USE AS MEDICAMENT

This invention relates to polyunsaturated fatty acid derivatives and their salts with tyrosine kinase inhibitor activity having the Formula (I)

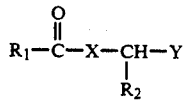

wherein
$R_1$ is an alkyl chain consisting of 18 to 24 carbon atoms containing at least two unsaturated double bonds;
X is selected from oxygen, imino group, or nitrogen substituted with alkyl consisting of 1 to 4 carbon atoms;
Y is hydrogen carboxyl, COOMe, or carboxamide group, where
Me is metal;
$R_2$ is either a side-group to the alpha carbon atom of any amino acid found in living organisms or a group having the formula (II)

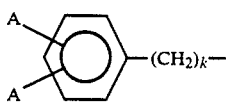

where
A is OH or one A is hydroxy and the other A is hydrogen, and k=0 or 1
or a moiety having the formula (III)

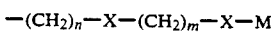

where
X is as described above,
n is an integer from 0 to 3, inclusive,
m is an integer from 0 to 4, inclusive,
M is either hydrogen or $R_1$—CO group where
$R_1$ is as described above.
or a chain having the Formula (IV)

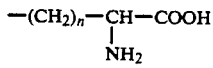

where
n is as defined above;
and to the method for preparation thereof.

Due to the immunostimulant and tyrosine kinase inhibitor activity, the compounds of the invention can be applied for stopping and suppressing the pathological cell proliferation, consequently, for treating the malignant neoplastic diseases.

According to recent investigations, the formation of malignant tumors is clearly the result of the abnormal activation of certain genes. The abnormal activation of these genes called proto-oncogenes and their transformation into oncogenes can be caused by several mechanisms independently of retroviruses. By definition, the term "oncogene" means that these genes permit the formation and survival of malignant neoplastic cells (Bradshaw, T.K.: Mutagenesis 1, 91–97 (1986).

In the present state of the art, the regulation of cell-division is carried out by a complex mechanism which consists of genomial information comprising proto-oncogenes and the finely adjusted interaction between different factors inducing growth and differentiation and endocrine and paracrine regulators. The close connection between oncogenes and growth factors is also supported by the fact that the major part of oncogenes encodes proteins which themselves are growth factors or growth factor receptors or which interact with the signal transduction mechanism induced by growth factors.

As each cell of an organism is part of a strictly regulated and systematic "cell society", it has long been presumed that, normally, cells only begin to divide as an effect of an extrinsic signal i.e. growth factor. Recent investigations have also provided that, in the permanently dividing neoplastic cells, a growth factor transduction pathway is always active but, in certain (pathological) cases, the exogene growth factor is replaced by an oncogene product [Winstein, B.; J. Cell. Biochem. 33, 213–224 (1987) and Paul, D.; Drug Res. 35, 772–779 (1985)].

Many of the consequent steps of the signal transduction mechanism are potential sites of oncogene intervention.

Under the physiological conditions of regulated cell-division such as embriogenesis or regeneration of injured tissue, proto-oncogenes which take part in the regulation of cell-division are activated by growth factors.

In transformed cells containing activated oncogenes, the complex interaction signals and regulating mechanisms which normally appear in a tissue have stronger effects because the organism and the microenvironment tend to control the cells that "break loose".

In the present state of the art, all the tumors are monoclonal, that is, they originate from one single transformed cell. Tumor progression begins when these transformed cells become able to divide permanently in this special, "hostile" microenvironment, and the divisions result in viable variants. To be able to survive and divide in this competitive environment, neoplastic cells have to possess special division parameters and other favorable features such as resistance to immune effects. Thus, in the permanently dividing neoplastic cells, there is a signal transduction mechanism constantly "on" which induces cell division and with which inhibitory regulating signals of the environment are unable to interact [Nicolson, G. L.: Cancer Research 47, 1473–1487 (1987)].

In the present state of the art, the regulation of cell division is carried out by three main transduction mechanisms: the stimulation or inhibition of the tyrosine kinase pathway, the phospholipid metabolism protein kinase C pathway, and/or the cAMP protein kinase A pathway.

The significance of the tyrosine kinase transduction pathway is demonstrated by the fact that a major part of the oncogenes encodes tyrosine kinases and that growth factor receptors and receptors of autocrine growth factors secreted by neoplastic cells are mainly tyrosine kinase as well [Yarden et al.: Ann. Rev. Biochem. 57, 443–478 (1988)].

Accordingly, it can be established that the key to the therapy of malignant tumors will be given by the knowledge and selective inhibition of the specific signal transduction mechanism used by the oncogenes and growth factors.

The aim of the invention is, therefore, to synthesize a novel tyrosine kinase inhibitor that stops and suppresses the pathological cell proliferation as well as prevents the development of malignant tumors by the inhibition of the activity of tyrosine kinase enzyme.

The invention is based on the discovery that the said purpose can be realized completely by the application of polyunsaturated fatty acid derivatives of the invention, having the above Formula (I) wherein $R_1$ is alkyl consisting of 18 to 24 carbon atoms containing at least two unsaturated double bonds;

X is selected from oxygen, imino, or nitrogen substituted with alkyl consisting of 1 to 4 carbon atoms;

Y is hydrogen, carboxyl, COOMe, or carboxamide group, where

Me is metal;

$R_2$ is either a side-group to the alpha carbon atom of any amino acid found in living organisms or a group having the above Formula (II) where A is Hydroxyl or one A is hydroxyl and the other A is hydrogen, and k=0 or 1, or a moiety having the above Formula (III) where X is as described above, n is an integer from 0 to 3, inclusive, m is an integer from 0 to 4, inclusive, M is either hydrogen or $R_1$—CO group where $R_1$ is as described above, or a chain having the above Formula (IV) where n is as defined above.

Further, the invention is based on the discovery that compounds having the above Formula (I) when incorporated into the membranes of tumor cells are able to inhibit the signal transduction mechanisms activated by oncogenes and growth factors, consequently, the pathological cell proliferation is suppressed.

Compounds having the above Formula (I) have not been known in the literature up to now.

The known related compounds contain saturated fatty acid residues as $R^1$ in the above Formula (I). These compounds are excellent as detergents and skin food ingredients, mainly in cosmetics, due to their hydrating capability and skin softening activity. For example, such agents are described in the Japanese Patent No. 58.168,696 or in the Eur. Pat. No. 139,481. Hiroshi et al. [Chem. Pharm. Bull. 35, 2935 (1987)] prepared palmitoyl serine applying to the preparation of liposomes. Several papers, such as Paquet et al. [Can. J. Biochem. 58, 573 (1980)] or Berger et al. [Tenside 23, 156 (1986)] covered the applications of palmitoyl threonine and palmitoyl methionine in the food industry.

It is worth to note that a fatty acylated derivative of diethylene triamine is described as one of the components of a chemically multicomponent system in the Hungarian Patent No. 4348/83, used for regeneration of neoplastic cells and tissues.

This invention, therefore, relates to the methods of preparing polyunsaturated fatty acid derivatives and their salts having the above Formula (I), wherein the substituents are as described above, comprising acylation of a compound having the Formula (VI)

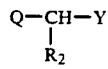  (VI)

where

Q is selected from hydroxyl, amino or NHR aminoalkyl groups with an alkyl group of 1 to 4 carbon atoms as R, Y and $R_2$ are as described above with a polyunsaturated fatty acid derivative having the Formula (V)

  (V)

where

Z is hydroxyl, halogen or $R_1$—COO with $R_1$ being either as described above or a halogen atom, in the presence of an acid absorbent.

In accordance with this invention, the acylating agents having the above Formula (V) can be prepared preferably from γ-linolenic acid (GLA) (18:3n-6(Z)-6,9-12-octadecatrienic acid) or from eicosapentaenic acid (EPA) (20:5ω-3(Z)-5,8,11,14,17) or from docosahexaenic acid (DHA) (22:6ω-3(Z)-4,7,10,13,16,19) as starting materials.

The main source of GLA may be the oil obtained from plant seeds, such as evening primrose (Oenothera biennis, Oenothera lamarkina) or Borago officinalis e.g. by the method of Brit. Pat. No. 2,183,635 or from the Tetrahymena ciliates by the method of French Pat. No. 2,574,089. As feedstocks for DHA and EPA or other typically $C_{18-24}\omega$-3 unsaturated fatty acids, oils from various salt-water and fresh-water fishes, mainly mackerels, cods, herrings, sardines, calamaries, Hypophthalmyctis and from their livers, such as cod-liver oil or shark-liver oil may be used.

Polyunsaturated carboxylic acids are transformed into acyl halides having the above Formula (V) by reacting them with inorganic acyl halides, such as $SOCl_2$, $POCl_3$, $PCl_3$, $PCl_5$ by any method well-known in the art of organic chemistry.

In the acylating reaction, polyunsaturated fatty acyl halides can be replaced by the corresponding anhydrides obtained by reacting the sodium salt of the corresponding fatty acid with said inorganic acyl halide.

The desired acylating agent may also be prepared directly from the carboxylic acid by any other methods known in the art of organic chemistry.

In the method of this invention, the acylating agents having the above Formula (V), prepared as above, are reacted with compounds having the above Formula (VI) to obtain compounds having the above Formula (I) through N-or O-acylating.

In the acylating reaction, organic bases such as pyridine or triethylamine are used as catalysts and acid absorbents. The reaction may be conducted at 10° to 120° C. with or without solvent. In some cases, the said organic bases may be used as solvents.

Since polyunsaturated fatty acid derivatives are immiscible with water, the acylating reaction may be conducted in the aqueous alkalic medium by the Schotten-Baumann's method.

The biochemical and biological features of compounds having the above Formula (I) are as follows:

The effect of compounds having the above Formula (I) on the enzymatic activity of tyrosine kinase was measured by the method of Schwarup et al. [J. Biol. Chem. 258, 10341-10347 (1984)] using treated and untreated rat spleen homogenisates.

For this test, 100 cm$^3$ of stock solution containing 50 millimoles of TRIS-Cl (at pH 7.8), 50 millimoles of magnesium chloride, 10 micromoles of sodium vanadate, 0.1 percent of Nonidet P-40 from Fluka A. G. Buchs, Switzerland), and 1 millimole of Angiotensin II was mixed with 60 mm$^3$ of rat spleen homogenisate. The reaction was started by the addition of 0.5 nanomole of ($^{32}$P)ATP. The reaction mixture was incubated at 30° C. for 10 min then the reaction was stopped by the addition of 150 mm$^3$ of 1 percent solution of trichloroacetic acid. 10 mm$^3$ of bovine serum albumine (at a concentration of 20 mg/cm$^3$) was added to the mixture and the precipitated protein was removed by centrifuging (3200 g for 25 min). 50 mm$^3$ aliquet of the supernatant liquid was dropped onto a Whatman P-81 phosphocellulose paper. The paper squares were washed six times with 0.5 percent phosphoric acid and once with acetone then dried. Their radioactivities were measured in 5 cm$^3$ of scintillation liquid. The results are collected in the following Table:

Test substrate: rat spleen homogenisate
Activities of spleens:
0.7135 pmole$^{32}$P/mg protein/min
1.0119 pmole$^{32}$P/mg protein/min
1.258 pmole$^{32}$P/mg protein/min

| Serial number | Materials tested Number of example | Amount (mm$^3$) | Activity pmole$^{32}$P/ mg/min | Tyrosine kinase activity (%) | Matter content (mg) |
|---|---|---|---|---|---|
| 1 | 2 | 3 | 4 | 5 | 6 |
| 1 | 24 C | 20 | 0.7932 | 100 | |
|   | 24 | 20 | a) 0.9527 b) 1.7148/1 mg | 120 | 1.8 |
|   | 24 C | 50 | 0.900 | 100 | |
|   | 24 | 50 | 0.1585 | 17.6 | 4.5 |
| 2 | 17 C | 20 | 0.8906 | 100 | |
|   | 17 | 20 | 0.0942 | 10.5 | 1 |
|   | 17 C | 50 | 0.885 | 100 | |
|   | 17 | 50 | 0 | 0 | 2.5 |
| 3 | C = compound of Example 17 | | | | |
|   | 16 | 20 | 0.043 | 4.8 | 1 |
|   | 16 | 50 | 0 | 0 | 2.5 |
| 4 | C = DMSO | | | | |
|   | 18 | 20 | 0.6917 | 62.18 | 1 |
|   | 18 | 20 | 0.3175 | 26.74 | 2.5 |
| 5 | C = DMSO | | | | |
|   | 20 | 20 | 0.4088 | 36.98 | 1 |
|   | 20 | 20 | 0 | 0 | 2.5 |
| 6 | 14 C | 20 | 1.1004 | 100 | |
|   | 14 | 20 | 0 | 0 | 1 |
|   | 14 C | 50 | 0.701 | 100 | |
|   | 14 | 50 | 0 0 | 2.5 | |
| 7 | 15 | 20 | 0.08512 | 7.735 | 1 |
|   | 15 | 50 | 0 | 0 | 2.5 |

C = control

The immunostimulating activity of compounds having the above Formula (I) was measured by the activation lymphocyte cells by virtue of polyclonal mytogenes as follows:

Two hundred thousand cells of a lymphocyte population obtained on Ficoll Uromiro gradient [A. Böyum: Scand. J. Clin. Lat. Invest. 21, 97 (1986)] were pipetted into the reservoirs of flat-bottom microplates to form 7 parallel cultures. 25 μg/cm$^3$ of Concanavalin A (Con A, Pharmacia, Sweden) was added to each sample. The control solution was 25 μg/cm$^3$ of Con A without any other ingredients. The plates were grown in an environment containing 5 percent of $CO_2$ at 37° C. for 72 hours. 8 hours before the end of growth, each sample was supplemented by 0.4 μCi of $^3$H-thymidine. After 72 hours, the cultures were filtered on a glass filter each. The filters were placed into scintillation cuvettes and 5 cm$^3$ of Liquifluor-containing toluene solution was added. The samples were measured in a Nuclear Chicago Isocap 300 beta counter and activities were read in count/min (cpm).

| Basic level: | Spontaneous 161 ± −19 | 5 μg/ml Con A 16387 ± −3017 | 25 μg/ml Con A 28419 ± −3967 |
|---|---|---|---|
| Product of Example 14 | | | |
| 0.1 μg/ml: p: | 179 ± −36 n.s. | 12287 ± −2480 0.01 | 30749 ± −4096 n.s. |
| 1.0 μg/ml: p: | 228 ± −48 n.s. | 13513 ± −2584 0.01 | 30728 ± −3691 n.s. |
| 10 μg/ml: p: | 183 ± −25 n.s. | 10078 ± −1951 0.01 | 25303 ± −3500 0.05 |
| Product of Example 16 | | | |
| 0.1 μg/ml: p: | 139 ± −21 n.s. | 12932 ± −2436 0.001 | 31470 ± −3960 0.05 |
| 1.0 μg/ml: p: | 219 ± −38 n.s. | 133010 ± −2560 0.02 | 32735 ± −4293 0.02 |
| 10 μg/ml: p: | 150 ± −25 n.s. | 10608 ± −2061 0.01 | 25551 ± −3791 n.s. |
| Product of Example 15 | | | |
| 0.1 μg/ml: p: | 151 ± −18 n.s. | 11759 ± −1735 n.s. | 27780 ± −3245 n.s. |
| 1.0 μg/ml: p: | 172 ± −26 n.s. | 12082 ± −2065 n.s. | 27106 ± −3296 n.s. |
| 10 μg/ml: p: | 158 ± −19 n.s. | 8336 ± −1452 0.05 | 20316 ± −2827 0.01 | c.p.m. average ± SEM
n = 12
n.s. = not significant

The active ingredients having the above Formula (I) may be processed into capsules, tablets or other known pharmaceutical formulations along with pharmaceutically acceptable carriers and/or additives in the usual pharmaceutical ways.

The principal advantages of the compounds and pharmaceutical preparations of this invention are as follows:

1. Through the inhibiton of the enzymatic activity of tyrosine kinase, a suppression of the signal transduction mechanisms activated by growth factors and/or oncogenes is provided leading to an inhibition of pathological cell proliferation processes.

2. The antioxidant and immunostimulating activity of the polyunsaturated fatty acid component gives a possibility to the complex tumor therapy.

3. Suppression of the pathological cell proliferation through the inhibition of tyrosine kinase is a much more gentle intervention than the conventional chemotherapy, such as a cytostatic treatment.

The following examples are presented to illustrate the method of this invention but are not intended to limit its scope.

EXAMPLE 1

Preparation of (Z)-5,8,11,14,17-eicosapentaenoyl chloride (EPA-Cl)

0.303 g (0.001 mole) of EPA was dissolved in 3 cm$^3$ of cyclohexane. The solution was placed into a round-bottom flask equipped with a loading funnel and 0.092 g of PCl$_3$, dissolved in 1 cm$^3$ of cyclohexane was introduced under a continuous N$_2$ stream at 50° C.

The mixture was stirred at room temperature for an hour. The reaction mixture was then clarified by activated charcoal and filtered. After evaporation, a yield of about 95 percent was obtained. Characteristic infrared absorption bands of the product: 1780 (CO), 1645 (C=C), 1460, 1400, 1370, 1340, 1290, 1240, 1170, 1095, 1015 cm$^{-1}$.

EXAMPLE 2

Preparation of (Z)-4,7,10,13,16,19-eicosahexaenoyl chloride (DHA Cl)

The same procedure as in Example 1 but EPA was replaced by 0.329 g (0.001 mole) of DHA.
Yield was about 94 percent.
Infrared bands: 1780 (CO) cm$^{-1}$.

EXAMPLE 3

Preparation of (Z)-6,9,12-octadecatrienoyl chloride (GLA-Cl)

The same procedure as in Example 1 but EPA was replaced by 0.278 g (0.001 mole) of GLA.
Yield was about 88 percent.
Infrared bands: 1780 (CO), 1650 (C=C) cm$^{-1}$.

EXAMPLE 4

Preparation of a mixture of polyunsaturated fatty acyl chlorides containing 30.5 percent of EPA-Cl and 49.1 percent of DHA-Cl 165 g (0.5 mole) of a mixture of polyunsaturated fatty acids containing 30.4 percent of EPA and 49.0 percent of DHA was dissolved in 500 cm$^3$ of cyclohexane. The solution was placed into a three-necked round-bottom flask equipped with a reflux condenser and a loading funnel and was heated to 60° C. with continuous stirring.

A tube filled with CaCl$_2$ was connected to the top of the condenser and a slow N$_2$ stream was applied. From the loading funnel, 45.8 g (0.33 mole) of PCl$_3$ was added dropwise to the solution with continuous stirring during a 1 to 1.5 hour period. After the introduction, the mixture was stirred for another 1 to 1.5 hours at 60° C. Deposited H$_3$PO$_3$ was removed from the cyclohexane solution by decantation. After clarification by activated charcoal, the solution was filtered then evaporated in vacuo. 166 g of acyl chloride was obtained at a yield of about 95 percent. Composition of the feedstock and the product was checked by HPLC.

EXAMPLE 5

Preparation of N-eicosapentaenoyl (4-hydroxyphenyl)-glycine 1.67 g (0.01 mole) of D,L-4-hydroxyphenyl glycine then 15 cm$^3$ of freshly distilled pyridine were placed into a round-bottom flask equipped with a reflux condenser and a loading funnel.

The mixture was heated to 60° to 65° C. and at this temperature, 3.85 g (0.012 mole) of EPA-Cl was introduced dropwise with continuous stirring during an hour. As the introduction had been finished, the reaction mixture was allowed to cool down and stirring was continued for 2 hours.

Pyridine was evaporated in vacuo, the residue was malaxated with water then extracted three times with ethyl acetate. The extract was washed twice with 0.5 percent hydrochloric acid then once with water, dried on dehydrated Na$_2$SO$_4$ and, finally, the solvent was evaporated.

Yield was about 78 percent.
Infrared bands: 1695 (C=0), 1620 (C=0 amide). 3200 (—NH, —OH) cm$^{-1}$.

Characteristic NMR signals in CDCl$_3$ to the amino acid moiety: 8.8 (bs) 3H, 6.9 (d) and 6.7 (d) 4H; to the fatty acid moiety: 5.35 (m), 2.85 (s), 2.50–1.40 (m), 0.98 (t) ppm.

EXAMPLE 6

Preparation of N-eicosapentaenoyl L-tyrosine

The same procedure as in Example 5 but D,D-4-hydroxyphenyl glycine was replaced by 1.81 g (0.01 mole) of L-tyrosine. Yield was about 62.5 percent.
Infrared bands: 1690 (CO), 1620 (CO amide), 3200 (—NH, —OH) cm$^{-1}$.

NMR signals in CDCl$_3$: 8.5 (bs) 3H, 6.7 (d) and 6.9 (d) 4H, 4.85 (q) 1H, 3.1 (d) 2H ppm while the signals to the fatty acid moiety were identical to those in Example 5.

EXAMPLE 7

Preparation of N-eicosapentaenoyl L-(3,4-dihydroxyphenyl-α-methyl)-alanine

The same procedure as in Example 5 but D,L-4-hydroxyphenyl glycine was replaced by 2.11 g (0.01 mole) of 3,4-dihydroxyphenyl-α-methylalanine.
Yield was about 63.5 percent.
Infrared bands: 1695 (CO), 1620 (CO amide), 3150 (—NH, —OH) cm$^{-1}$.

NMR signals in CDCl$_3$: 8.8 (bs) 4H, 6.50 (c) and 6.62 (s) and 6.75 (d) 3H, 5.0 (q) 1H, 3.15 (dd) 2H ppm.

The signals to the fatty acid moiety were identical to those in Example 5.

EXAMPLE 8

Preparation of N-docosahexaenoyl (4-hydroxyphenyl)-glycine

The same procedure as in Example 5 but EPA-Cl was replaced by 4.16 g (0.012 mole) of DHA-Cl prepared as in Example 2. Yield was about 72.5 percent. IR and NMR spectra were identical to those in Example 5.

EXAMPLE 9

Preparation of N-docosahexaenoyl L-tyrosine

The same procedure as in Example 5 but 1.81 g (0.01 mole) of L-tyrosine was used as the amino acid component and EPA-Cl was replaced by 4.16 g (0.012 mole) of DHA-Cl. Yield was about 64.7 percent. IR and NMR spectra were identical to those in Example 6.

EXAMPLE 10

Preparation of N-docosahexaenoyl L-3,4-dihydroxyphenyl-α-methyl)-alanine

The same procedure as in Example 5 but 2.11 g (0.01 mole) of L-methyl dopa was used as amino acid and EPA-Cl was replaced by 4.16 g (0.012 mole) of DHA-Cl.

Yield was about 65.6 percent.
IR and NMR spectra were identical to those in Example 7.

EXAMPLE 11

Preparation of N-octadecatrienoyl (4-hydroxyphenyl)-glycine

The same procedure as in Example 5 but EPA-Cl was replaced by 3.56 g (0.012 mole) of GLA-Cl prepared as in Example 3. Yield was about 73.8 percent. IR and NMR spectra were identical to those in Example 5.

EXAMPLE 12

Preparation of N-octadecatrienoyl L-tyrosine

The same procedure as in Example 5 but 1.81 g (0.01 mole) of L-tyrosine was used as amino acid and EPA-Cl was replaced by 3.56 g (0.012 mole) of GLA-Cl. Yield was about 64.7 percent.

IR and NMR spectra were identical to those in Example 6.

EXAMPLE 13

Preparation of N-octadecatrienoyl L-(3,4-dihydroxy-phenyl-α-methyl)-alanine

The same procedure as in Example 5 but 2.11 g (0.01 mole) of α-methyl dopa was used as amino acid and EPA-Cl was replaced by GLA-Cl. Yield was about 61.3 percent.

IR and NMR spectra were identical to those in Example 7.

EXAMPLE 14

Acylating of (4-hydroxyphenyl)-glycine

The same procedure as in Example 5 but EPA-Cl was replaced by 4.2 g (0.012 mole) of the mixture of polyunsaturated fatty acyl chlorides as prepared in Example 4. Yield of the mixed product was about 88 percent, containing N-eicosapentaenoyl (4-hydroxyphenyl)-glycine and N-docosahexaenoyl (4-hydroxyphenyl)-glycine as the main components.

Infrared bands: 1695 (CO), 1620 (CO amide), 3200 (—NH, —OH) cm$^{-1}$.

NMR signals in CDCl$_3$: 8.5 (bs) 3H, 6.9 (d) and 6.7 (d) 4H, 5.35 (m) 11H, 2.85 (s) 9H, 2.5–1.5 (m) 8H, 0.98 (t) 3H characteristic to the fatty acid.

EXAMPLE 15

Acylating of L-tyrosine with the mixture of Example 4

The same procedure as in Example 5 but 1.81 g (0.01 mole) of L-tyrosine was used as amino acid and EPA-Cl was replaced by 4.2 g of the mixture of polyunsaturated fatty acyl chlorides as prepared in Example 4. Yield of the mixed product was about 66.2 percent, containing N-eicosapentaenoyl tyrosine and N-docosahexaenoyl tyrosine as the main components.

Infrared bands: 1680, 1620, 3150 cm$^{-1}$.

NMR signals in CDCl$_3$: 8.50 (bs) 3H, 6.90 (d) 4H, 6.70 (d), 4.85 (q) 1H, 3.10 (d) 2H ppm.

Signals characteristic to the fatty acic moiety were identical to those in Example 14.

EXAMPLE 16

Acylating of L-serine with the mixture of Example 4

The same procedure as in Example 5 but 0.01 mole of L-serine was used as amino acid and 0.012 mole of the mixture of polyunsaturated fatty acyl chlorides prepared in Example 4 was applied as fatty acyl chloride. Yield of the mixed product was about 56.7 percent. containing N-eicosapentaenoyl L-serine and N-docosahexaenoyl L-serine as the main components.

Infrared bancs: 1890, 1620, 3150 cm$^{-1}$.

NMR signals in CDCl$_3$: 9.40, 8.40, 3.95 (s) 1H each, 4.50 (m) 1H, 3.90 (dd) 2H.

Signals characteristic to the fatty acid moiety were identical to those in Example 5.

EXAMPLE 17

Acylating of L-threonine

The same procedure as in Example 5 but 0.01 mole of L-threonine was used as amino acid and 0.012 mole of the mixture of polyunsaturated fatty acyl chlorides prepared in Example 4 was applied as fatty acyl chloride. Yield of the mixed product was about 62.5 percent. containing N-eicosapentaenoyl L-threonine and N-docosahexaenoyl L-threonine as the main components.

Infrared bands: 1690 (CO), 1620 (CO amide), 3150 (—NH, —OH) cm$^{-1}$.

NMR signals in CDCl$_3$: 7.35 (bs) 3H, 4.50 (c) 1H, 4.40 (m) 1H, 1.20 (d) 3H ppm, characteristic to the amino acid residue. Signals to the fatty acid moiety were identical to those in Example 5.

EXAMPLE 18

Acylating of L-ornithine.HCl

The same procedure as in Example 5 but 1.63 g (0.01 mole) of L-ornithine hydrochloride was used as amino acid and 0.012 mole of the mixture of polyunsaturated fatty acyl chlorides prepared in Example 4 was applied as fatty acyl chloride. Yield of the mixed product was about 45.5 percent, containing N$^2$-eicosapentaenoyl L-ornithine. HCl and N$^2$-docosahexaenoyl L-ornithine.HCl as the main components.

Infrared bands: 1690 (CO), 3100 (—NH), 1630 (C=O amide) cm$^{-1}$.

NMR signals characteristic to the amino acid moiety in CDCl$_3$: 8.30–7.30 (bs) 5H, 4.50 (m) 1H, 3.25 (m) 2H, 2.35 (m) 2H, 1.60 (m) 2H ppm.

EXAMPLE 19

Acylating of L-lysine.HCl

The same procedure as in Example 5 but 1.83 g (0.01 mole) of L-lysine hydrochloride was used as amino acid and 0.012 mole of the mixture of polyunsaturated fatty acyl chlorides prepared in Example 4 was applied as fatty acyl chloride. Yield of the mixed product was about 43.2 percent, containing N$^2$-eicosapentaenoyl L-lysine.HCl and N$^2$-docosahexaenoyl L-lysine.HCl as the main components.

Infrared bands: 1690 (CO), 1630 (CO amide), 3150 (—NH) cm$^{-1}$.

NMR signals in CDCl$_3$: 8.30–7.30 (bs) 5H. 4.50 (m) 1H, 3.25 (m) 2H, 2.30 (m) 2H, 1.50 (m) 4H ppm.

EXAMPLE 20

Acylating of L-arginine.HCl

The same procedure as in Example 5 but 2.11 g (0.01 mole) of L-arginine hydrochloride was used as amino acid and the mixture of polyunsaturated fatty acyl chlorides prepared in Example 4 was applied as fatty acyl chloride. In the extraction step, ethyl acetate was replaced by n-butanol. Yield of the mixed product was about 57.1 percent, containing N$^2$-eicosapentaenoyl L-arginine.HCl and N$^2$-docosahexaenoyl L-arginine.HCl as the main components.

Infrared bands: 1695 (CO), 1625 (CO amide), 3200 (—NH, —OH) cm$^{-1}$.

NMR signals in CDCl$_3$: 8.50 (bs) and 7.60 (bs) and 6.80 (bs) 7H, 4.40 (bs) 1H, 3.30 (bs) 2H, 1.50 (m) 4H ppm.

Signals characteristic to the fatty acid moiety were identical to those in Example 5.

EXAMPLE 21

Acylating of α-methyl dopa

The same procedure as in Example 5 but 2.11 g (0.01 mole) of (3,4-dihydroxyphenyl-α-methyl)-alanine was used as amino acid and the mixture of polyunsaturated fatty acyl chlorides prepared in Example 4 was applied as fatty acyl chloride. Yield of the mixed product was about 67.8 percent, containing N-eicosapentaenoyl α-methyl-dopa and N-docosahexaenoyl α-methyl-dopa as the main components.

NMR signals characteristic to the amino acid moiety in CDCl$_3$: 8.80 (bs) 4H, 6.75 (d) and 6.62 (s) and 6.50 (d) 3H, 5.00 (q) 1H, 3.15 (dc) 2H.

Signals characteristic to the fatty acid moiety were identical to those in Example 5.

EXAMPLE 22

Acylating of diethylene triamine 2.12 g (0.04 mole) of diethylene triamine, 8.88 g (0.088 mole) of triethylamine and 150 cm$^3$ of anhydrous toluene were placed into a four-necked roundbottom flask. The mixture was heated to 85° to 90° C. then 29.08 g (0.08 mole) of the mixture of fatty acyl chlorides prepared as in Example 4 was added dropwise with continuous stirring. The mixture was continuously stirred at this temperature for 4 hours then 2.9 g (0.008 mole) of the said fatty acyl chloride mixture was additionally cropped in and stirring was continued for 2 hours more.

Precipitated triethylamine hydrochloride was filtered at room temperature and filtrate was evaporated under N$_2$ atmosphere at 4000 N/m$^2$. The residue was washed with petroleum ether. Yield of the mixed product was about 62.4 percent, containing N,N'-[bis(aminoethylene-imino]bis-cocosahexaenoate and N,N'-[bis(aminoethylene)-imino]bis-eicosapentaenoate as the main components.

Infrared bands: 1645 (CO amide), 3250 (—NH) cm$^{-1}$.

NMR signals in CDCl$_3$: 3.55 (m) 8H (N—CH$_2$—) ppm and twice of the signals characteristic to the fatty acid moiety as in Example 5.

EXAMPLE 23

Acylation of diethanolamine 2.83 g (0.02 mole) of diethanolamine hydrochloride then 15 cm$^3$ of dioxane were placed into a roundbottom flask equipped with a reflux condenser and a loading funnel. The mixture was heated to 55° to 60° C. and 13.6 g (0.04 mole) of the mixture of fatty acyl chlorides prepared as in Example 4 was added at that temperature during a 1 hour period.

The reaction mixture was continuously stirred for 2 hours followed by evaporation at a pressure of 5400 N/—$^2$. The residue was washed with petroleum ether. Yield of the mixed product was about 92.6 percent, containing 0,0'-(diethanolamine)-bis-docosahexaenoate. HCl and 0,0-(diethanolamine)-bis-docosahexaenoate. HCl as the main components.

Infrared bancs: 1720 (CO ester), 3100 (—NH) cm$^{-1}$.

NMR signals in CDCl$_3$: 10.0 (s) 1H, 4.0–4.4 (m) 4H, 3.3–3.7 (m) 4H ppm.

Signals characteristic to the fatty acid moiety were identical to those in Example 5.

EXAMPLE 24

Acylation of L-lysine 5.61 g (0.034 mole) of L-lysine monohydrate was dissolved in 150 cm$^3$ of distilled water in a round-bottom flask equipped with magnetic stirrer. The solution was heated to 80° C. and, with continuous stirring, Cu(OH)$_2$.CuCO$_3$.xH$_2$O was added in small portions until it appeared to be dissolved. The possible excess of Cu(OH)$_2$.CuCO$_3$.xH$_2$O, remained after stirring for 15 minutes, was filtered out. The solution was cooled to room temperature with continued stirring and 1.8 g (0.017 mole) of Na$_2$CO$_3$ then 12.2 g (0.034 mole) of the mixture of fatty acyl chlorides prepared as in Example 4 were added dropwise. After 1-hour stirring, the acylated copper complex precipitate was filtered then washed once with methanol and several times with water until a colorless was liquor had been obtained. In a round-bottom flask, 200 cm$^3$ of methanol was added to the copper complex and the complex was decomposed by bubbling gaseous H$_2$S through the mixture.

the reaction mixture was filtered and the solvent was evaporated under N$_2$ atmosphere at a pressure of 5400 N/m$^2$ not above 50° C. The residue was washed with petroleum ether, malaxated with acetone, filtered and dried under N$_2$ atmosphere in both cases. Yield of the mixed product was 17.24 percent.

M.p.: 116° C. (with decomposition).

N$^6$-eicosapentaenoyl L-lysine and N$^6$-docaso-hexaenoyl L-lysine were the main components of the product.

|   | Calculated | Found |
|---|---|---|
| C | 73.12 | 72.98 |
| H | 9.71 | 9.92 |
| N | 6.33 | 6.18 |

EXAMPLE 25

Preparation of N$^5$-docosahexaenoyl L-ornithine

The same procedure as in Example 24 out L-lysine was replaced by 0.034 mole of L-ornithine and the mixture of acyl chlorides was replaced by DHA-Cl prepared as in Example 2. Yield was about 15.6 percent.

|   | Calculated | Found |
|---|---|---|
| C | 73.30 | 72.84 |
| H | 9.50 | 9.61 |
| N | 6.33 | 6.51 |

EXAMPLE 26

Preparation of N$^6$-docosahexaenoyl L-lysine

The same procedure as in Example 24 but the mixture of acyl chlorides was replaced by DHA-Cl prepared as in Example 2. Yield was 20.42 percent.

|   | Calculated | Found |
|---|---|---|
| C | 73.68 | 74.13 |
| H | 9.65 | 9.72 |

| | Calculated | Found |
|---|---|---|
| N | 6.14 | 6.22 |

What is claimed is:

1. A method of inhibiting tyrosine kinase activity in an animal subject which comprises the step of administering to said subject a therapeutically effective amount of a compound of the Formula (I)

$$R_1-\overset{O}{\underset{}{C}}-X-\overset{}{\underset{R_2}{C}H}-Y \qquad (I)$$

wherein $R_1$ is an alkyl chain consisting of 18 to 24 carbon atoms containing at least two unsaturated double bonds;

X is oxygen, imino group, or a nitrogen substituted with an alkyl group consisting of 1 to 4 carbon atoms;

Y is hydrogen, carboxyl, COOMe where Me is metal or carboxamide group; and $R_2$ is either a side-group to the alpha carbon atom of any amino acid except L-Glu or L-Asp found in the living organisms or a group having the Formula (II)

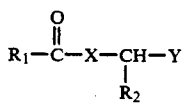

where

A is a hydroxyl or one A is hydroxyl and the other A is hydrogen, and k=0 or 1, or a moiety having the Formula (III), $$-(CH_2)_n-X-(CH_2)_m-X-M \qquad (III)$$

where

X is as described above, n is an integer from 0 to 3, inclusive, m is an integer from 0 to 4, inclusive, M is either hydrogen or $R_1$—CO group where $R_1$ is as described above; or a chain having the formula (IV), $$-(CH_2)_n-\underset{NH_2}{\overset{}{C}H}-COOH \qquad (IV)$$

where n is as defined above.

2. A method of inhibiting tyrosine kinase activity in an animal subject which comprises the step of administering to said subject a therapeutically effective amount of a compound of the Formula (I)

$$R_1-\overset{O}{\underset{}{C}}-X-\overset{}{\underset{R_2}{C}H}-Y \qquad (I)$$

wherein $R_1$ is an alkyl chain consisting of 18 to 24 carbon atoms containing at least two unsaturated double bonds;

X is an imino group;

Y is carboxyl; and $R_2$ is a side-group to the alpha carbon atom of an amino acid selected from the group consisting of L-Tyr, L-Ser, L-Thr, L-Orn, L-Lys, and L-Arg.

3. The method of inhibiting tyrosine kinase activity defined in claim 2 wherein $R_2$ is the side chain to the alpha carbon atom of L-tyrosine in the compound of the Formula (I).

4. The method of inhibiting tyrosine kinase activity defined in claim 2 wherein the compound of the Formula (I) is selected from the group consisting of N-eicosapentaenoyl tyrosine, N-docosahexaenoyl tyrosine, and a mixture thereof.

* * * * *